United States Patent [19]
Miller et al.

[11] 4,059,007
[45] Nov. 22, 1977

[54] CONVECTIVE AIR FLOW DYNAMIC CALORIMETER

[75] Inventors: Bernard Miller, Princeton, N.J.; J. Ronald Martin, Easton; Charles H. Meiser, Jr., Yardley, both of Pa.; Harold W. Lambert, Pennington; Harry Buvel, Trenton, both of N.J.

[73] Assignee: Textile Research Institute, Princeton, N.J.

[21] Appl. No.: 767,730

[22] Filed: Feb. 11, 1977

[51] Int. Cl.² .................................................. G01K 17/00
[52] U.S. Cl. ............................... 73/190 R; 23/253 PC
[58] Field of Search ............... 73/15 R, 15.4, 190 R, 73/190 CV; 23/253 PC

[56] References Cited

U.S. PATENT DOCUMENTS 2,026,179  12/1935  Keith ........................................ 73/190
2,764,021  9/1956  Sims et al. ................................ 73/190

Primary Examiner—Herbert Goldstein
Attorney, Agent, or Firm—John J. Kane; Frederick A. Zoda; Albert Sperry

[57] ABSTRACT

A calorimeter which measures a naturally induced flow of incoming air in a horizontal entry duct (air-inlet chamber) and through a horizontal elbow duct to an upright straight flue used as a combustion chamber, the measuring system consisting of a thermistor version of a hot-wire anemometer, a bridge circuit with a matched thermistor, and a strip chart recorder, the calorimeter utilizing convective air flow to make practical a method for directly, continuously, and quantitatively measuring, over the entire period of combustion from ignition to extinguishment, the heat emitted by a burning test material positioned in the upright vertical flue, thus providing a realistic, sensitive, and accurate method for monitoring quantities such as the total heat emitted per unit mass of sample, the total heat emitted per unit mass of volatilized portion, the maximum emitted energy flux, and the average burning acceleration, the apparatus being particularly useful for continuously evaluating burning behavior, particularly of flexible sheet materials such as textiles, plastics, and films.

12 Claims, 8 Drawing Figures

U.S. Patent  Nov. 22, 1977  4,059,007
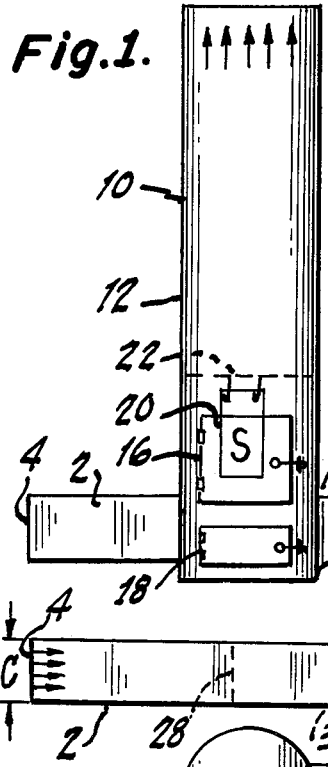
Fig.1.
Fig.2.
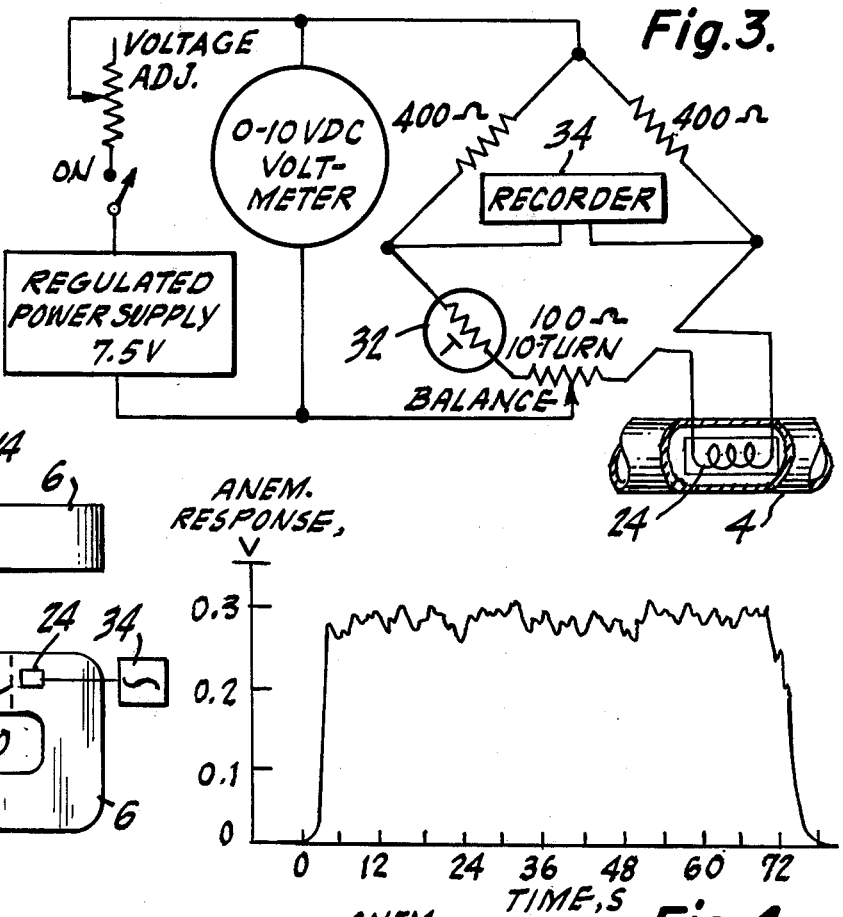
Fig.3.
Fig.4.
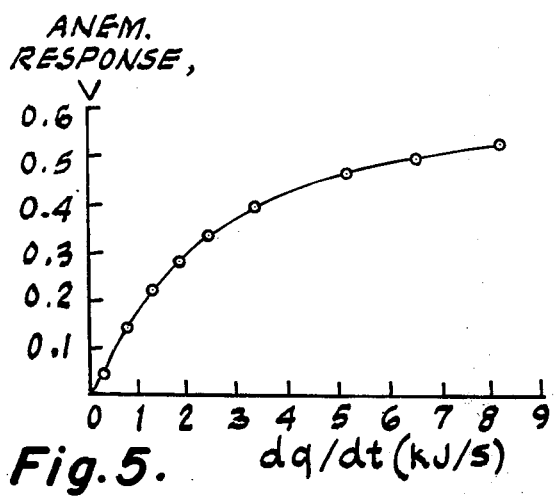
Fig.5.
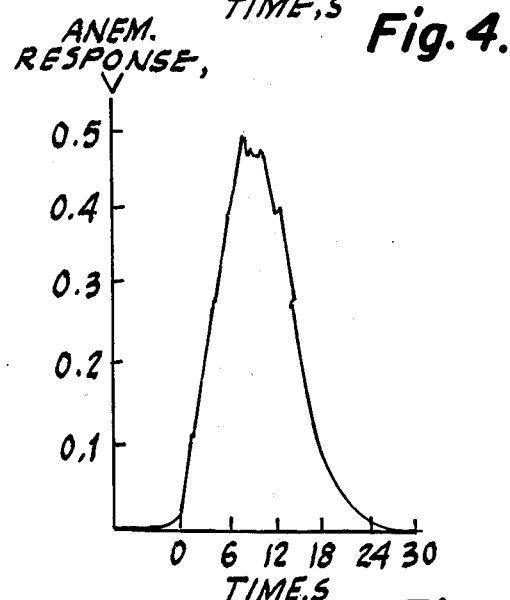
Fig.6.
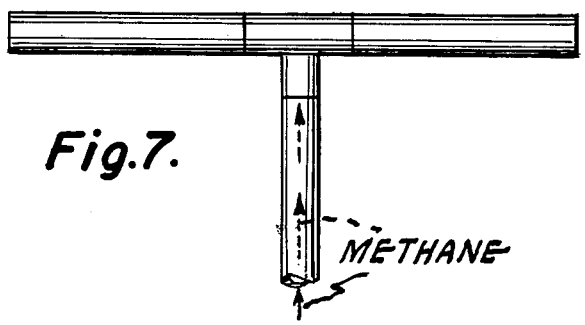
Fig.7.
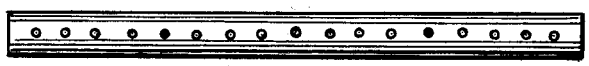
Fig.8.

CONVECTIVE AIR FLOW DYNAMIC CALORIMETER

BACKGROUND OF THE INVENTION

1. Field of the Invention

This invention relates to the field of equipment used to measure calorimetric flammability characteristics, particularly the heat emission, of materials such as plastic rods, foam, films and products made from fibers, such as paper and textile structures, especially fabrics.

Heat emission is a major hazard in uncontrolled burning, all too often causing death, serious injury, and extensive damage, particularly from accidental fires. Rate of heat emission determines whether a material will self-extinguish once ignited, because a sufficient rate of heat feedback is necessary to maintain burning, particularly of a fabric. The extent to which the flammability hazard of a material can be understood and eventually be minimized is dependent on our ability to measure heat emission accurately. In addition to the important consideration of safety, the amount of heat emitted and the rate of heat emission can indicate more precisely than any other factors the progress and the completeness of the burning process.

2. Description of the Prior Art

Despite the importance of being able to make meaningful calorimetric measurements in order to understand the burning characteristics of materials, various types of such measuring equipment heretofore provided have had many disadvantages and shortcomings. Arrangements for monitoring burning have depended on measuring the heat transferred to a specific target or to a relatively large heat sink surrounding the burning sample. In the former case, the result is strongly dependent on the location of the target with respect to the flame, an arbitrary as well as variable factor. Using an enveloping heat sink (e.g., as in the form of a labyrinth) requires imposing artificial restraints upon the testing environment such as forced air flow, limited sample size, and restricted freedom of choice of test conditions.

The other general type of arrangement has allowed the heat to remain in the gas stream flowing away from the burning material, and provided for this heat to be measured by following the temperature rise of the gas with a detector that is an insignificant heat sink. But calorimetry based on such gas temperature measurements has not been of practical value, since it requires that the air-flow rate be kept constant, thus imposing unnatural and undesirable restrictions. In summary, devices which have depended on heat transfer have inherent complications which inhibit their use for the study and evaluation of, for example, burning textiles. Direct measurement of emitted heat would be preferable to indirect measurement involving transferred heat. Combustion calorimeters also have the drawback of burning the material under highly artificial conditions as compared to conditions relating to the natural, self-sustained flaming of organic solids. Such artificial conditions confine the spatial configuration and impose an unnatural atmosphere, casting doubt and uncertainty upon the interpretation and significance of results.

SUMMARY OF THE INVENTION

The convective air flow dynamic calorimeter of the present invention includes a combustion chamber for holding therein a material or other sample to be tested for the burning characteristics thereof. To facilitate entry and exit of the testing samples into the combustion chamber at least one or more access doors will be configured in the walls of the combustion chamber. Air is supplied to the combustion chamber through an air inlet opening which is positioned at the external ambient environment. Air is carried from the air inlet opening through an air inlet duct and preferably through an elbow duct to a position for direct entry into the combustion chamber. Extending vertically from the combustion chamber is a vertically extending flue which aids in the exhausting of air from the combustion chamber during testing.

The burning characteristics of the sample are monitored by a unique sensing method which includes the use of a hot wire anemometer sensing means or thermistor within the air inlet flow ducting. A second thermistor is positioned in the external ambient environment to be utilized as a standard against which the resistance reading of the first thermistor will be compared. The comparison of these resistance readings is achieved through the use of an electrical bridging circuit and a recording means located therein.

The bridging circuit indicates the difference in resistance readings between the first thermistor located within the ducting and the second thermistor located in the external ambient environment. Prior to the initiation of burning a variable balancing resistor is utilized to balance the bridging circuit. Once burning has been initiated the convective induced flow of air upward through the flue induces the flow of air through the air inlet opening and past the first thermistor. The resulting reduction in temperature of the first thermistor will show in the bridging circuit as a reduction in resistance of the first thermistor and will be indicated by the bridge circuit means on the recording device. In this manner the various characteristics of burning of the test sample can be accurately sensed and fully recorded.

To minimize the flow of extraneous air current by the first thermistor an air restriction means such as course screens or the like may be positioned within the air inlet flow ducting between the air inlet opening and the location of the first thermistor. In this manner the thermistor will be reduced in temperature only responsive to the flow of air thereby which is induced by the burning characteristics of the sample being tested.

To facilitate the calibration of the air flow detector with respect to burning characteristics a calibration device such as a T-shaped methane gas burner may be utilized. In this manner the anemometer response may be calibrated against the heat energy produced within the burning chamber in order to fully calibrate the calorimeter of the present invention.

It is an object of the present invention to provide equipment that enables direct and continuous measurement to be made of the rate of heat emission from a burning material over the entire period of combustion of a test material;

It is an object of the present invention to provide equipment that enables a variety of related energy quantities to be determined under conditions that closely resemble natural burning under "real fire" conditions;

It is an object of the present invention to provide equipment that enables variations in sample size, shape, configuration, orientation, or degree of restraint to be imposed without requiring changes in the basic arrangement of the testing structure;

It is an object of the present invention to provide a realistic, sensitive, and accurate method for monitoring the burning behavior of textiles, films, plastics, papers, and other types of organic solids;

It is an object of the present invention to provide an instrument that gives an immediate quantitative response to any increase or decrease in burning rate;

It is an object of the present invention to provide an apparatus that is designed so that no sensing or measuring element or transducer is located where it will be affected by combustion products, whether they be thermal or chemical in nature; and It is an object of the present invention to provide equipment that is simple to construct, easy to operate, and readily maintained in working order.

BRIEF DESCRIPTION OF THE DRAWINGS

While the invention is particularly pointed out and distinctly claimed in the concluding herein, a preferred embodiment is set forth in the following detailed description which may be best understood when read in connection with the accompanying drawings, in which:

FIG. 1 is a front elevation of an embodiment of the calorimeter of the present invention;

FIG. 2 is a top plan view of the embodiment shown in FIG. 1;

FIG. 3 is a schematic drawing of an embodiment of the circuit and bridge circuit means of the present invention;

FIG. 4 is a graph of the voltage drop of the anemometer versus time for the calibration device burning at a constant fuel feed rate;

FIG. 5 is a calibration curve showing the anemometer response to rate of energy output;

FIG. 6 is a graph showing the anemometer response with respect to time for a typical burning textile or fabric;

FIG. 7 is a front plan view of an embodiment of the calibration device of the present invention; and FIG. 8 is a top plan view of the embodiment shown in FIG. 7.

DETAILED DESCRIPTION OF THE PREFERRED EMBODIMENT

In that form of the invention chosen for purposes of illustration in the drawing figures, the present invention includes a horizontal entry duct 2 leading from the air inlet opening 4 to an elbow duct 6 which in turn leads to an upright straight flue 8 extending vertically and used as a burning chamber.

The dimensions of the convective air flow dynamic calorimeter indicated in FIGS. 1 and 2 meet the requirements of sensitivity and practicality for use with textile materials, but for other applications the basic apparatus may be scaled up or down as desired to meet special needs and circumstances in testing.

The air inlet chamber 2, the elbow duct 6, and the vertical flue 8 may be constructed from cylindrical sections of standard galvanized heating duct units, such as are obtainable at commercial hardware supply stores. These units need not be permanently attached to each other, thereby making it convenient to remove them for occasional cleaning. During operation the joints between the sections are sealed with tape. Three sections, for example each 0.6 meter in length, make up the flue 8. The two upper sections 10 and 12 may be water-cooled by means of 6.4-millimeter one-quarter-inch) outside-diameter copper tubing (not shown) soldered to their external surfaces (about 15 m of tubing per section). During measurements, water flow is maintained at about 20 cubic centimeters per second. The combustion chamber of lowest section 14 of the straight flue 8 has an upper access door 16 and a lower access door 18. Door 16 may have a viewing window and supplies access for conveniently mounting a sample 20 or S extending downward from a horizontal suspension wire 22 by small hooks. The lower door 18 is used for recovering unburned residues. Both doors can be gasketed to prevent air leaks into the burning chamber.

The entry duct 2 and the elbow duct 6 are horizontally oriented in order to prevent extraneous air currents produced by the sensing thermistor 24 which is a heat source. The curvature of the elbow duct 6 prevents flame radiance from disturbing the air-flow transducer, the thermistor 24, which may be centrally mounted along the axis of the entry duct 2 near the junction with the elbow duct 6. Curvature of the duct 6 also contributes to compactness of the apparatus. Positioned within the duct 2 between inlet 4 and thermistor 24 may be one or more coarse, wire mesh screens 28 and 30 which suppress the effects of external air currents. The plane of each screen 28 and 30 is preferably perpendicular to the axis of the air inlet chamber 2 to minimize extraneous air current.

The diameter of the inlet duct 2 and of the elbow duct 6 can be about half of the diameter of the combustion chamber 14 so that the resulting air velocities are high enough to measure accurately and the degree of restriction does not affect burning behavior.

The incoming air flow rate is monitored by a version of a hot-wire anemometer, which detects the rate of air flow by the extent to which it is cooled below its static operating temperature. This unit uses a thermistor 24 for this purpose of comparing dynamic and static conditions. A second thermistor 32 (FIG. 3) is located in the electric bridge circuit outside of the chamber to compensate for any changes in ambient temperature and humidity. An applied bridge potential of 6.0 volts serves to supply current to heat the matched thermistor pair 24 and 32. The output of the bridge is fed to a strip chart recorder 34, which may have a full-scale range of 1 volt.

In calibrating the equipment described, a heat source with a known, adjustable rate is required to convert observed air flow rates to heat fluxes. A methane gas flame is suitable for this purpose. A T-shaped methane burner (FIGS. 7 & 8) is mounted in the burning chamber at a point corresponding to the vertical midpoint of the space set aside for the test sample 20. The burner should have the same width as a fabric sample, such as 150 mm. Methane is metered to this burner at rates ranging from 8 to 400 cubic centimeters per second, which correspond to a heat flux range from about 0.3 to 14.0 kilojoules per second (alternatively expressed as 0.3 to 14.0 kilowatts). This range is sufficient to cover the heat emission behavior of commonly tested ignitable textile materials. After a specific methane flow rate has been established, the gas is ignited and the air flow rate is recorded for about one minute. A typical calibration run of the response for methane burning at a constant fuel-feed rafte is illustrated in FIG. 4. The unevenness of the anemometer response voltage over most of the time of the run is a true record of the velocity of the air passing the detector, and is typical of turbulent gas flow. The average voltage value can be obtained simply by eye, or by any other signal-averaging method. An example of a complete calibration curve relating to anemometer response to heat flux is shown in FIG. 5. This curve can be used directly to convert anemometer output voltage to an instantaneous rate of heat emission $dq/dt$ measured in $kJ/s$ or $kW$ for any time during burning.

When a fabric sample 20 burns, it produces an air flow trace on the strip chart recorder 34, such as the typical response for a burning fabric shown in FIG. 6. The peak value corresponds to the maximum rate of heat emission achieved by the sample. The total amount of heat emitted by a sample can be obtained by integrating the rates of heat emission over the time of burning, that is, calculating the area under the curve and converting this measurement into a quantity of heat, $q$. Numerical integration can be simplified by converting the calibration curve, as illustrated in FIG. 5, to an analytical expression which can be programmed into a computer so that successively entered values of anemometer output can be conveniently converted to rates of heat emission and integrated over the time of burning.

An analytical expression for the calibration curve in FIG. 5 can consist of two independent parts; a linear portion describing the calibration at low heat emission levels (for anemometer outputs less than 0.2 volt in this case) and a parabolic portion for higher levels. The latter can be fitted by parabolic regression to an equation of the form.

$$dq/dt = AV^2 + BV + C \quad \text{(Equation 1)}$$

were A, B, and C are constants, and where V is the anemometer output voltage.

The linear portion of the curve of the type illustrated by FIG. 5 may be fitted by eye (to pass through the origin and to be continuous with the curve of Equation 1) to an equation of the form $$dq/dt = KV \quad \text{(Equation 2)}$$

where $K$ is a constant.

The total heat $q$ given off during burning is obtained by computing the average rates of heat emission over small time intervals (using whichever of the above equations applies) and numerically integrating the following expression:

$$q = \int \frac{dq}{dt} dt = \Sigma \frac{1}{2} \left[ \frac{dq}{dt_n} + \frac{dq}{dt_{n+1}} \right] (\Delta t) \quad \text{(Equation 3)}$$

In operating the calibrated equipment for making emitted heat measurements on a sample, such as a fabric specimen 150 mm wide and 300 mm long, the specimen can be suspended from the horizontal wire 22 by small hooks with its long dimension in the vertical direction in the combustion chamber 14. A sheet of aluminum foil is placed on the bottom of the chamber adjacent to door 18 to catch any unburned residue that falls. The voltage supply to the bridge circuit (FIG. 3) is brought to a value of 6.0 volts and the bridge circuit is balanced to produce a zero voltage output on the strip chart recorder 34. The sample is ignited in whatever manner desired (for example, with a small pilot flame) and both doors 16 and 18 are closed. Within a few seconds the combustion in chamber 14 and the upward movement of air therein will cause the horizontal movement of air through ducts 2 and 6. This movement of air past thermistor 24 will cause an anemometer response indicating the progress of burning and producing a curve on the strip chart recorder 34 similar to that shown in FIG. 6. From the response curve, voltage against time in $s$, the following values may be obtained:

1. The maximum heat emission rate, expressed in $kJ/s$, or alternatively, the maximum emitted heat flux, expressed in $kW$ (obtained from the peak anemometer response).

2. The average burning acceleration, expressed in $kJ/s^2$ (the maximum rate divided by the time from the first response to peak).

3. The total heat emitted per unit mass of sample, as in $MJ/kg$ (determined from integration of the overall response curve).

4. The total heat emitted per unit mass of volatilized sample, expressed in $MJ/kg$ (by taking into account the mass of the residue, including whatever fell to the bottom of combustion chamber 14 onto the aluminum foil).

Each material being studied may be run in triplicate to show consistency in results. Subsequent runs can be made as soon as the anemometer response has returned to zero.

Any configuration of fabric can be studied with this procedure.

If a frame or other mounting accessory with appreciable mass is to be included in the combustion chamber 14, a new calibration should be carried out to take into account the thermal and gas-flow restriction of the cross-sectional area thereof.

The equipment of the present invention may be used in determining the burning characteristics of practically any type of combustible material including textile materials formed from any of the naturally occurring and man-made fibers as well as mixtures or blends of such fibers. Also, plastic films, sheets and rods, paper, felts, floor coverings, rubber sheeting, rigid and flexible foams, plastic screen, flexible plywood, laminated materials, and flammable liquids on inert substrates may be evaluated with respect to their caloric properties during burning by means of the present invention.

While particular embodiments of this invention have been shown in the drawings and described above, it will be apparent, that many changes may be made in the form, arrangement and positioning of the various elements of the combination. In consideration thereof, it should be understood that preferred embodiments of this invention disclosed herein are intended to be illustrative only and not intended to limit the scope of the invention.

We claim:

1. A convective air flow dynamic calorimeter, for measuring the heat emission of a burning sample, comprising:
   a. a combustion chamber for holding therein a sample to be tested for burning characteristics thereof;
   b. an air inlet opening positioned at the external ambient environment;
   c. an air inlet duct extending to said combustion chamber from said air inlet opening to provide a supply of air to said combustion chamber;
   d. air outlet means extending from said combustion chamber to provide a path of exhaust therefrom; and
   e. anemometer sensing means positioned between said air inlet opening and the location of the test sample in said combustion chamber to sense the air flow therethrough said flowrate being a measure of the heat emission of the burning sample.

2. The calorimeter as defined in claim 1 wherein said anemometer sensing means comprising a first thermistor.

3. The calorimeter as defined in claim 2 further comprising a second thermistor positioned in the external ambient environment, and further comprising an electrical bridge circuit means which includes said first thermistor and said second thermistor to indicate the difference in resistance values therebetween which indicates the air flow rate through the calorimeter.

4. The calorimeter as defined in claim 3 including a recording means electrically connected in said electrical bridge circuit means to show the difference in resistance values between said first thermistor and said second thermistor over a period of time.

5. The calorimeter as defined in claim 4 including a variable resistance balancing means to balance the voltage drop across said bridge circuit prior to initiation of burning of the test sample within said combustion chamber.

6. The calorimeter as defined in claim 1 wherein said combustion chamber comprises a vertically extending flue.

7. The calorimeter as defined in claim 1 wherein said combustion chamber includes door access means therein to facilitate placement therein and removal therefrom of samples to be tested.

8. The calorimeter as defined in claim 1 further comprising an elbow duct positioned between said air inlet duct and said combustion chamber to minimize extraneous air currents in the calorimeter.

9. The calorimeter as defined in claim 1 further comprising air flow restriction means in said air inlet duct to minimize extraneous air currents therethrough.

10. The calorimeter as defined in claim 1 further comprising a calibration device for placement within said combustion chamber to calibrate said anemometer, said calibration device comprising:
   a. a hollow vertical conduit adapted to receive a combustible gas therethrough;
   b. a horizontal hollow duct being capped at both ends and secured to the upper end of said vertical conduit to form a T-shaped construction to allow gas flow therethrough; and
   c. a plurality of gas discharge holes in said horizontal conduit to allow the controlled discharge of gas therefrom for burning.

11. A convective air flow dynamic calorimeter, for measuring the heat emission of a burning sample, comprising:
   a. a combustion chamber extending vertically for holding therein a sample to be tested for burning characteristics thereof, said chamber including door access means to facilitate placement and removal of samples;
   b. an air inlet opening positioned at the external ambient environment;
   c. an air inlet duct extending to said combustion chamber from said air inlet opening to provide a supply of ambient air to said combustion chamber;
   d. an elbow duct means connecting said air inlet duct to said combustion chamber;
   e. air outlet means extending from said combustion chamber to provide a path of exhaust therefrom;
   f. air flow restriction means in said air inlet duct to minimize extraneous air currents therethrough;
   g. a first thermistor to act as an anemometer sensing means positioned between said air inlet opening and the test sample in said combustion chamber to sense the air flow therethrough;
   h. a second thermistor positioned in the external ambient environment; and
   i. an electrical bridge circuit means for comparing the resistance values of said first thermistor and said second thermistor to indicate the flow of air through the calorimeter said flowrate being a measure of the heat emission of the burning sample.

12. The calorimeter as defined in claim 11 wherein said electrical bridge circuit means includes a recorder means for illustrating the burning characteristics of the tested samples.

* * * * *